United States Patent [19]
Baba et al.

[11] 4,241,082
[45] Dec. 23, 1980

[54] AGENTS FOR PROMOTING REPRODUCTIVE ABILITY OF DOMESTIC ANIMALS

[75] Inventors: Yoshihiko Baba; Hiroyoshi Horikoshi, both of Tokyo, Japan

[73] Assignee: Sankyo Company Limited, Tokyo, Japan

[21] Appl. No.: 935,266

[22] Filed: Aug. 21, 1978

[30] Foreign Application Priority Data

Sep. 2, 1977 [JP] Japan .................................. 52-105702
Jan. 27, 1978 [JP] Japan .................................... 53-7996

[51] Int. Cl.³ .................. A61K 31/24; A61K 31/22; A61K 31/195
[52] U.S. Cl. .................................. 424/309; 424/311; 424/319

[58] Field of Search ................ 424/319, 330, 309, 311

[56] References Cited

PUBLICATIONS

Raziano et al.—Chem. Abst. vol. 75, (1971) p. 95076Q.
Dolbeneva—Chem. Abst. vol. 79, (1973) p. 77294N.
Tanimura—Chem. Abst. vol. 68, (1968) p. 94603C.

*Primary Examiner*—Frederick E. Waddell
*Attorney, Agent, or Firm*—Frishauf, Holtz, Goodman & Woodward

[57] ABSTRACT

New use of L-dopa or its derivative in combination with a specific amino acid, optionally together with an L-dopa-antimetabolite, as agents for promoting a reproductive ability in domestic animals suffering from reproductive disorders.

13 Claims, No Drawings

AGENTS FOR PROMOTING REPRODUCTIVE ABILITY OF DOMESTIC ANIMALS

This invention relates to a new use of a combination of L-dopa or its derivatives, optionally together with an L-dopa-antimetabolite, with a specific amino acid as an agent for promoting the reproductive ability of a domestic animal suffering from a reproductive disorder.

More particularly, it is concerned with a composition for promoting the reproductive ability of a domestic animal suffering from a reproductive disorder which comprises as an active ingredient L-dopa or its derivatives in combination with a specific amino acid, optionally together with an L-dopa-antimetabolite, and a veterinarilly acceptable carrier.

In breeding of domestic animals and poultry such as beef cattle, dairy cattle, pig, chicken and the like, there have recently been encountered an increasing number of breeding disorders and other factors causing a decrease in the conception rate, as over-crowded breeding or dependence on an artificial diet increases. Accordingly, a countermeasure to such problems is becoming more and more important. In the reproduction of pluriparous domestic animals, in particular, decrease in the conception rate, decrease of the litter sizes (the number of egg-laying), various types of breeding disorders or the like may compel the animals to become subjects to be slaughtered, based on the economics because of the reduced rate of reproduction. In these cases, a prophylactic treatment against these disorders may be of great value as well, together with a palliative treatment against apparent (exhibited) disorders.

It is also extremely important to ensure the reproduction of such animals, whose pedigree is highly esteemed, as race horses or pet dogs, as well as to regulate the egg-laying conditions for certain kind of fish, whose eggs are difficult to collect, in the fish farming extensively carried on nowadays. Furthermore, some of the experimental animals (including specifically diseased animals) employed for developing drugs or other purposes show an extremely low reproduction rate, and the problem of improving the reproductive efficiency of such animals is an urgent problem.

For the purpose of promoting reproduction as well as treating the breeding disorders of domestic animals, there has usually been applied, together with an attempt to improve a breeding control, optionally and symptomically a pharmaceutical preparation of a proteinous hormone such as various kinds of gonadotropins, especially HCG (human chorionic gonadotropin), PMS (pregnant mare serum gonadotropin) or the like, and a steroidal hormone such as estrogen, progesterone or the like. Also, it is disclosed and claimed in co-pending Japanese Patent Application No. 132271/1975 (provisionally published on May 11, 1977 under No. 57330/1975) that L-dopa (l-3,4-dihydroxyphenylalanine), one of the biological substances other than gonadotropins, sexual hormones and the like, or a derivative of L-dopa exhibits an extremely remarkable activity for improving in the reproduction efficiency. And further, it is disclosed and claimed in co-pending Japanese Patent Application No. 37957/1976 (provisionally published on October 15, 1977 under No. 122630/1977) that the said activity of L-dopa can be remarkably enhanced by a combined use of L-dopa with a substance, which is capable of inhibiting the in vivo degradation of L-dopa and of potentiating the long-lasting action of L-dopa in a living body (hereinafter referred to as L-dopa-antimetabolite).

On the other hand, it is usually said that fewer cases of breeding disorders in male domestic animals are observed as compared with female domestic animals. However, there are often encountered cases in which an expensive breeding male animal does not function, contrary to expectation, and becomes therefore useless in an early stage, bringing about lowering of the economical efficiency in reproduction of the domestic animal.

The male breeding disorders often appear as decline or extinction of the sexual desire, abnormality of the sperm, abnormality of the genital organs, especially testis or epididymis, or the like, and as causes of such disorders may be attributed various factors such as the endocrine system, age, season, nutrition, controlling of breeding conditions and the like. And further, the selective breeding, for example, of cattle based on milk producibility, meat producibility and the like has been continuously carried out for a long range of time, and this has brought more frequent occurrence of problems relating to reproducibility as compared with the cases for the crossbred cattle. The same problems have also been occurring in the experimental animals employed for developing drugs as a result of their specialization of pure line breeding.

There has been found heretofore no decisive treatment for these problems as seen in female cases. For example, an optional and symptomatic administration of testosterone, HCG (human chorionic gonadotropin), PMS (pregnant mare serum gonadotropin) or the like has usually been supplied, but satisfactory results have not been achieved yet.

In view of the technical state in the prior art as depicted above and also from the standpoint to further enhance the promising activity of L-dopa or its derivative for promoting a reproductive efficiency, together with the possible decrease in cost of an agent of this type, especially for reduction in the amount of the expensive L-dopa-antimetabolite, the present inventors have made earnest studies to improve an L-dopa agent for promoting a reproductive efficiency and, as a result, found that the activity of L-dopa or its derivative can be remarkably enhanced by a combination thereof with one or more of the specific amino acids selected from the group consisting of L-arginine, L-ornithine, L-lysine, D-phenylalanine, L-glutamic acid and γ-aminobutyric acid, together with a marked reduction in a dose of L-dopa or its derivative, and also that the activity of the said combination of L-dopa or its derivative with the amino acid can be further enhanced by the addition of the L-dopa-antimetabolite. The present invention has thus been completed upon these findings.

It is, accordingly, a primary object of this invention to provide a practically effective veterinary composition for promoting reproductive efficiency in male and female domestic animals.

Other objects and advantages of this invention will be more fully apparent to those skilled in the art from the following description.

The L-dopa-antimetabolite as used herein is intended to include various dopa decarboxylase inhibitors known per se such as, for example, L-α-hydrazino-3,4-dihydroxy-α-methyl-β-phenylpropionic acid, N-DL-seryl-N'-(2,3,4-trihydroxybenzyl)hydrazine and the like.

According to some examples of the embodiments of this invention, the group of female mice, which were in their best period for reproduction and medicated with a combination of L-dopa or its derivative and the L-dopa-antimetabolite, showed an improved conception rate as compared with another group of mice medicated with L-dopa alone. An excellent conception rate was observed in a group of mice of about 10 months old, which experienced a reproduction test four times and failed to conceive at the fourth test, after being medicated with a combination of L-dopa or its derivative and, further, an inducing effect for egg-laying has also been recognized in chickens in the moulting season as well in the chickens, quails or the like with a lowered egg-laying for some reasons or other.

In comparative studies between a medicated group of L-dopa and a group of L-dopa plus L-arginine using male rabbits which did not show any mating behaviors despite their reaching the age of sexual maturity, there was observed a significant improvement in the group in which L-arginine was co-used. Furthermore, by co-administration of L-dopa and L-arginine to a pig from which collection of the sperm had been impossible, it became possible to collect sperm which is employable for artificial insemination, and this improvement was found to continue even after cessation of the medication.

The agent for promoting reproduction of animals according to the invention may be administered through either oral or parenteral route. For oral administration, the agent may be mixed with the diet and, in this case, a special pharmaceutical preparation such as microcapsule may be employed. Parenteral administration may be preferably carried out particularly through a subcutaneous or intramuscular injection without critical limitation. The pharmaceutical preparations adopted for both oral and parenteral administrations may also contain excipients, solubilizing agents, antioxidants and the like.

The dose of the main active ingredient, L-dopa or its derivative, may vary depending upon the kind, symptome, body weight and other factors of the domestic animal to be treated, but it is usually about 0.2 mg to 50 mg/kg at one administration and may be given in a single daily dosage form or several divided forms. In case of the administration in admixture with a conventional feed stock, L-dopa or its derivative may be usually contained at a concentration of about 0.1 to 2% by weight upon the finished feed.

The amino acid, preferably L-arginine or D-phenylalanine, may be employed and blended with the main active ingredient, usually and preferably within a range from 1/10 to 10 times the amount of L-dopa or its derivative employed, while the L-dopa-antimetabolite may be applied usually and preferably within a range from 1/100 to 10 times the amount of L-dopa or its derivative employed.

In the present invention, there may be used not only L-dopa but also an L-dopa derivative, and the following are representative examples of the L-dopa derivative.

I. 3,4-Diacyl derivatives of L-dopa and the salts thereof

For example,
(1) 3,4-diacetyloxy-L-phenylalanine hydrochloride

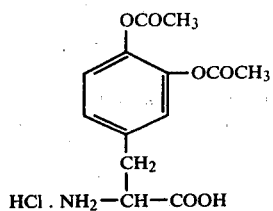

(2) 3,4-dipivalyloxy-L-phenylalanine perchlorate

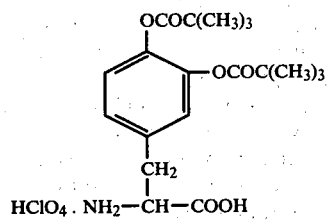

II. Carboxy esters of L-dopa or the 3,4-diacyl derivatives thereof and the salts thereof For example,
(1) 3,4-dihydroxy-L-phenylalanine methyl ester hydrochloride

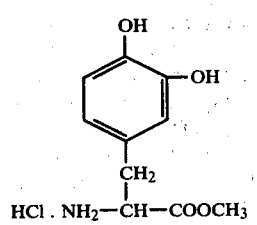

(2) 3,4-diacetyloxyl-L-phenylalanine methyl ester hydrochloride

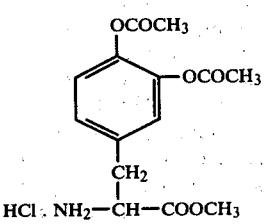

p1 (3) 3,4-dihydroxy-L-phenylalanine benzyl ester hydrochloride

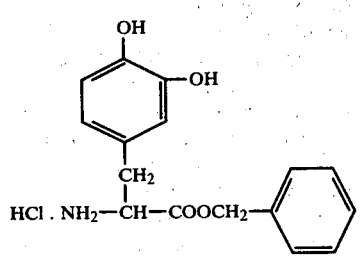

(4) 3,4-diacetyloxy-L-phenylalanine benzyl ester hydrochloride

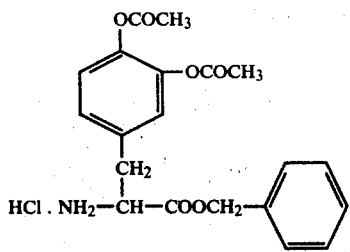

(5) glycyl-3,4-diacetyloxy-L-phenylalanine methyl ester hydrochloride

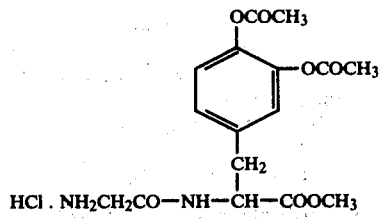

III. Enamine derivatives of L-dopa or the 3,4-diacyl derivatives thereof

For example,
(1) 3,4-dipivalyloxy-N-(1-methyl-2-acetylvinyl)-L-phenylalanine pivaloyloxymethyl ester

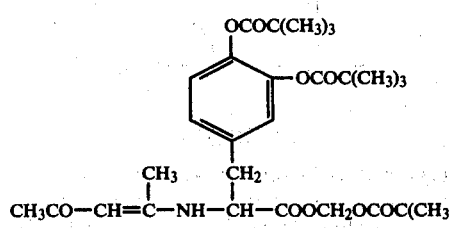

(2) 3,4-dipivalyloxy-N-(1-methyl-2-acetylvinyl)-L-phenylalanine potassium salt

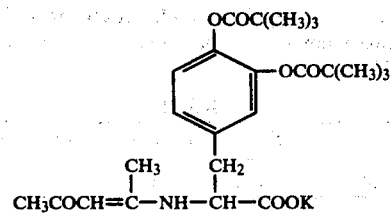

(3) 3,4-diacetyloxy-N-(1-methyl-2-acetylvinyl)-L-phenylalanine potassium salt

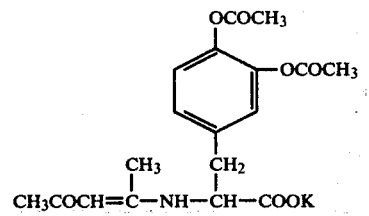

IV. Amido derivatives of L-dopa or the 3,4-diacyl derivatives thereof

For example,
(1) N-formyl-3,4-dipivalyloxy-L-phenylalanine

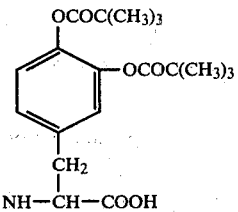

(2) N-formyl-3,4-dipivalyloxy-L-phenylalanine pivalyloxy-L-phenylalanine pivaloyloxymethyl ester

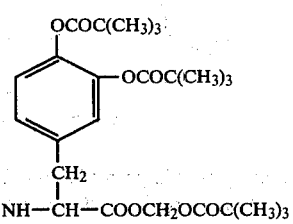

(3) N-formyl-3,4-diacetyloxy-L-phenylalanine

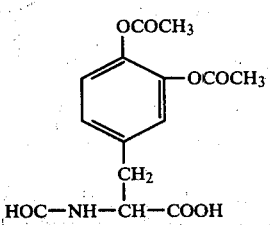

(4) N-formyl-3,4-diacetyloxy-L-phenylalanine potassium salt

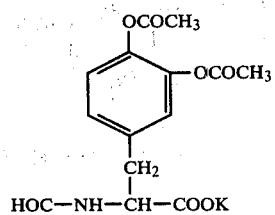

(5) glycyl-3,4-diacetyloxy-L-phenylalanine hydrochloride

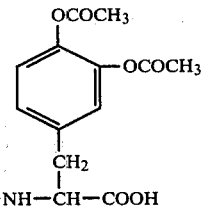

(6) 3,4-diacetyloxy-L-phenylalanylglycine hydrochloride

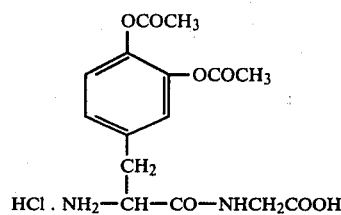

V. Dipeptides of L-dopa and the derivatives thereof

For example, (1) 3,4-dihydroxy-L-phenylalanyl-3,4-dihydroxy-L-phenylalanine hydrochloride

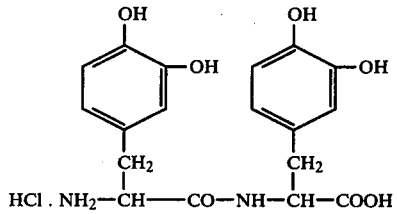

(2) 3,4-diacetyloxy-L-phenylalanyl-3,4-diacetyloxy-L-phenylalanine methyl ester hydrochloride

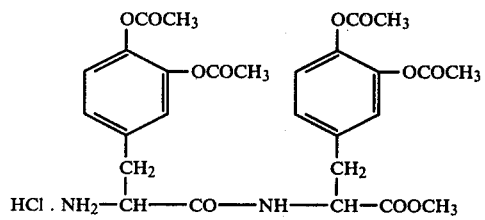

(3) 3,4-diacetyloxy-L-phenylalanyl-3,4-diacetyloxy-L-phenylalanine benzyl ester hydrochloride

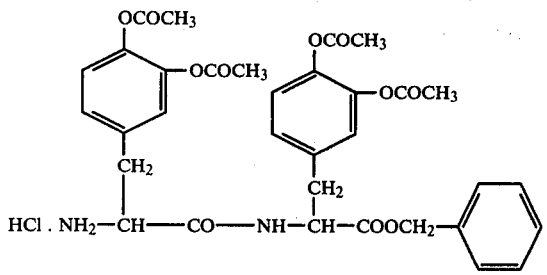

VI. Dipeptides of L-dopa and other natural α-amino acids

For example, (1) L-tyrosyl-L-dopa

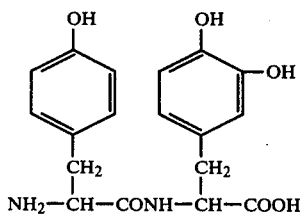

(2) glycyl-3,4-diacetyloxy-L-phenylalanine benzyl ester hydrochloride

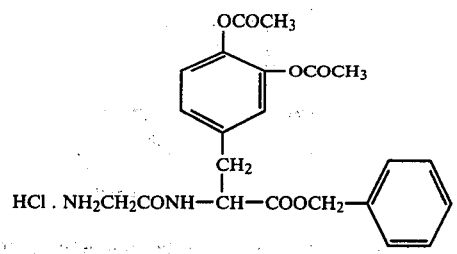

(3) L-leucyl-L-dopa

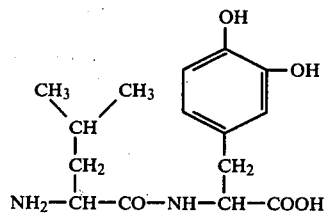

(4) L-dopa-D-alanine

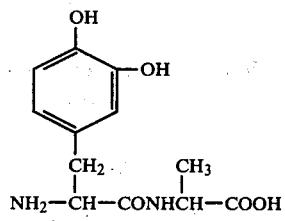

EXAMPLE 1

To female mice of 7-weeks of age which were in their best period for reproduction, the drugs were given through intraperitoneal injection twice a day for 5 days, and they were thereafter caged together with male mice for 20 days. One male mouse was provided to two female mice and the male mouse was exchanged twice during the course of the experiment. The states of conception were examined through laparotomy 25 days after commencement of the medication. Results are shown in Table 1.

TABLE 1

| Drug medicated | Number of animal | Number of pregnant | Conception rate (%) | Number of uterine disorder |
|---|---|---|---|---|
| I Non-medicated group | 33 | 20 | 60.6 | 4 |
| II L-dopa 10 mg/kg/once | 22 | 16 | 72.7 | 1 |
| III L-dopa 10 mg/kg/once + L-arginine 10 mg/kg/once | 20 | 18 | 90 | 1 |
| IV L-dopa 10 mg/kg/once + D-phenylalanine 10 mg/kg/once | 20 | 19 | 95 | 0 |

EXAMPLE 2

Female mice (about 10 months of age) which had experienced a reproduction test four times and failed to conceive at the fourth test, were picked up and the experiments were carried out according to the same way as described in Example 1. Male mice employed were those in their best period for reproduction. Results are shown in Table 2.

TABLE 2

| | Drug medicated | Number of animal | Number of pregnant | Conception rate (%) |
|---|---|---|---|---|
| I | Non-medicated group | 12 | 4 | 33 |
| II | L-dopa 10mg/kg/once | 8 | 6 | 75 |
| III | L-dopa 10mg/kg/once + L-arginine 10 mg/kg/once | 6 | 5 | 83 |
| IV | L-dopa 10mg/kg/once + D-phenylalanine 10mg/kg/once + L-arginine 10mg/kg/once | 6 | 6 | 100 |
| V | L-dopa 10mg/kg/once + L-α-hydrazino-3,4-dihydroxy-α-methyl-β-phenylpropionic acid 10mg/kg/once | 6 | 6 | 100 |
| IV | L-dopa 10mg/kg/once + γ-aminobutyric acid 10mg/kg/once | 4 | 4 | 100 |

In the present experiments there was observed no uterine disorder in all cases.

EXAMPLE 3

As breeding male animals for reproduction, there were selected eight male rabbits which had not shown any mating behavior or had finally not come into mating because of feeble mating behavior, when caged several times together with female rabbits. According to the observed conditions, they were separated into two groups of each four. The group I received 10 mg/kg of L-dopa and the group II received 10 mg/kg of L-dopa and 10 mg/kg of L-arginine intramuscular injection once a day for four days. Three to four hours after every injection, rabbits of each group were placed together with parous female rabbit for 30 minutes to observe their behavior. Three hours after injection of the fourth day, there were observed that all of the rabbits in the group I began to show mating behavior but only intermittently, and mating was ultimately not effected, while those in the group II exhibited very positive mating behavior and mating was also effected in two animals. The effect of co-use of L-arginine has thus been recognized.

EXAMPLE 4

The effect of the drugs on the spermatogenesis of male rat was examined. Male rat of 25 days of age were separated into four groups, each consisting of ten animals. To host animals were given the drugs intraperitoneally twice a day for eight days. At the tenth day the animals were sacrificed to carry out the histological examination of testis.

The testis of each animal was fixed in formalin immediately after removal and sections were prepared by staining with hematoxylin and eosin according to the usually way.

The cross section of the semiferous tubule of each preparation was microscopically examined under the magnifying power of 400. For classifying the cross sections into the I, II or III stage, whose definition will be given later, 20 sections of the semiferous tubule were examined randomly each out of the specimen obtained from right and left testis of the same animal and, therefore, a total of 40 sections of the semiferous tubule in the testis of one animal were examined. The examination was performed independently by two examiners and the estimation as to an individual animal was done by the mean value of results obtained by the two examiners. Results thereby obtained are shown in Table 3, in which the estimation is expressed by a mean value of a group of ten animals.

TABLE 3

| | Estimation* | | |
|---|---|---|---|
| Treatment | I stage | II stage | III stage |
| Non-medicated group | 17.0 + 1.4 | 7.2 + 0.2 | 16.1 + 1.1 |
| L-dopa 10mg/kg/once | 12.8 + 1.5 | 7.7 + 1.4 | 19.3 + 1.1 |
| L-dopa 10mg/kg/once + L-arginine 10mg/kg/once | 10.1 + 1.7 | 7.2 + 0.9 | 23.1 + 1.2 |
| L-dopa 30mg/kg/once + L-arginine 30mg/kg/once | 12.0 + 1.2 | 7.5 + 0.8 | 20.5 + 1.0 |

*Criteria for estimation:
I stage; the case in which the primary spermatocyte can be seen in the semiferous tubule.
II stage; the case in which the secondary spermatocyte or the spermatid can be seen in a small number.
III stage; the case in which the spermatid can be seen predominantly and in a large number.

EXAMPLE 5

To a male pig (Hampshire strain; body weight, 200 kg) from which the sperm could not be collected although the age had already been in a suitable period, 2.0 g of L-dopa and 2.0 g of L-arginine were given orally over a 15-days period. One week after cessation of the medication the pig was approached to a estrous female pig and he repeatedly showed mating behaviors and succeeded in mating. Furthermore, the sperm could be collected several times thereafter.

EXAMPLE 6

To a male pig (Hampshire strain; body weight, 170 kg) which was the same conditions as described in Example 5, were orally given 1.7 g of L-dopa and 1.7 g of L-arginine over a 15-days period. The pig became active in some degree as compared with the state before medication and began to mount a female dummy and bare the testis. About one month after cessation of the medication, the sperm could be collected using a female dummy in an amount of 100–240 ml every time. The artificial insemination was successfully carried out with the sperm thus collected.

EXAMPLE 7

To a triparous cow (Holstein strain; 4 years of age), which had not clearly shown a normal estrus even after 5 months from parturition, namely under a feeble estrus, 2 mg/kg of body weight of L-dopa and 2 mg/kg of L-arginine were once injected subcutaneously. On the 4th day from the administration, a manifest estrous sign or estrous behavior was observed and the artificial insemination was then carried out. After about 4 months from the insemination, pregnancy was confirmed.

EXAMPLE 8

To a triparous cow (Holstein strain; 4 years of age), which has not shown a normal estrus even after 7 months from parturition and had been diagnosed as having ovarian atrophy, 2 mg/kg of body weight of L-dopa and 2 mg/kg of body weight of L-arginine were once injected subcutaneously. On the 5th day from the administration, appearance of follicle within ovary was observed by palpation and on the 11th day an estrous sign was developed. After 2 days from the developed estrous sign, the artificial insemination was carried out. After about 2 months therefrom, pregnancy was confirmed.

It will be apparent from the above test results that a remarkable promoting effect for reproductive efficiencies can be attained according to this invention in domestic animals suffering from a reproductive disorder. As also apparent from the above Examples, the term "a reproductive disorder" as used herein with respect to female domestic animals is intended to generally include various common disorders such as ovarian cyst, ovarian hypoplasia, ovarian senescence, hypovaria, ovarian atrophy, feeble estrus, anaphrodisia and repeat breeder and the like.

What is claimed is:

1. A veterinary composition for promoting a reproductive ability of a domestic animal suffering from a reproductive disorder which contains an active component in an amount effective to promote said reproductive ability, said active ingredient comprising component (i) L-3,4-dihydroxyphenylalanine or a pharmaceutically acceptable substituted L-3,4-dihydroxyphenylalanine, and component (ii) at least one amino acid selected from the group consisting of L-arginine, L-ornithine, L-lysine, D-phenylalanine, L-glutamic acid and γ-aminobutyric acid, the ratio of said amino acid to said said L-3,4-dihydroxyphenylalanine or derivative thereof being between 1:10 and 10:1, and a veterinarily acceptable carrier said pharmaceutically acceptable substituted L-3,4-dihydroxyphenylalanine being selected from the group consisting of
3,4-diacetyloxy-L-phenylalanine hydrochloride,
3,4-dipivalyloxy-L-phenylalanine perchlorate,
3,4-dihydroxy-L-phenylalanine methyl ester hydrochloride,
3,4-diacetyloxy-L-phenylalanine methyl ester hydrochloride,
3,4-dihydroxy-L-phenylalanine benzyl ester hydrochloride,
3,4-diacetyloxy-L-phenylalanine benzyl ester hydrochloride,
glycyl-3,4-diacetyloxy-L-phenylalanine methyl ester hydrochloride,
3,4-dipivalyloxy-N-(1-methyl-2-acetylvinyl)-L-phenylalanine pivaloyloxymethyl ester,
3,4-dipivalyloxy-N-(1-methyl-2-acetylvinyl)-L-phenylalanine potassium salt,
3,4-diacetyloxy-N-(1-methyl-2-acetylvinyl)-L-phenylalanine potassium salt,
N-formyl-3,4-dipivalyloxy-L-phenylalanine,
N-formyl-3,4-dipivalyloxy-L-phenylalanine pivalyloxy-L-phenylalanine pivaloyloxymethyl ester,
N-formyl-3,4-diacetyloxy-L-phenylalanine,
N-formyl-3,4-diacetyloxy-L-phenylalanine potassium salt, glycyl-3,4-diacetyloxy-L-phenylalanine hydrochloride,
3,4-diacetyloxy-L-phenylalanylglycine hydrochloride,
3,4-dihydroxy-L-phenylalanyl-3,4-dihydroxy-L-phenylalanine hydrochloride,
3,4-diacetyloxy-L-phenylalanyl-3,4-diacetyloxy-L-phenylalanine methyl ester hydrochloride,
3,4-diacetyloxy-L-phenylalanyl-3,4-diacetyloxy-L-phenylalanine benzyl ester hydrochloride,
L-tyrosyl-3,4-dihydroxyphenylalanine,
glycyl-3,4-diacetyloxy-L-phenylalanine benzyl ester hydrochloride,
L-leucyl-3,4-dihydroxyphenylalanine, and
L-3,4-dihydroxyphenylalanine-D-alanine.

2. A composition according to claim 1 which also contains an L-3,4-dihydroxyphenylalanine decarboxylase inhibitor in a ratio of said L-3,4-dihydroxyphenylalanine or derivative thereof of between 1:100 and 10:1.

3. A composition according to claim 2 wherein said inhibitor is L-α-hydrazino-3,4-dihydroxy-α-methyl-δ-phenylpropionic acid or N-DL-seryl-N'-(2,3,4-trihydroxybenzyl)hydrazine.

4. A composition according to claim 1 wherein said active ingredient is contained in an amount of 0.1 to 2% of said composition.

5. A composition according to any one of claims 1, 2, 3, or 4 wherein said component (i) is L-3,4-dihydroxyphenylalanine and said component (ii) is L-arginine or D-phenylalanine.

6. A method for promoting a reproductive ability of a domestic animal suffering from a reproductive disorder which comprises orally or parenterally administering (i) L-3,4-dihydroxyphenylalanine or a pharmaceutically acceptable substituted L-3,4-dihydroxyphenylalanine, together with (ii) at least one amino acid selected from the group consisting of L-arginine, L-ornithine, L-lysine, D-phenylalanine, L-glutamic acid and γ-aminobutyric acid, the ratio of said amino acid to said L-3,4-dihydroxyphenylalanine or derivative thereof being between 1:10 to 10:1 to the host animal in an amount sufficient to promote said reproductive ability said pharmaceutically acceptable substituted L-3,4-dihydroxyphenylalanine being selected from the group consisting of
3,4-diacetyloxy-L-phenylalanine hydrochloride,
3,4-dipivalyloxy-L-phenylalanine perchlorate,
3,4-dihydroxy-L-phenylalanine methyl ester hydrochloride,
3,4-diacetyloxy-L-phenylalanine methyl ester hydrochloride,
3,4-dihydroxy-L-phenylalanine benzyl ester hydrochloride,
3,4-diacetyloxy-L-phenylalanine benzyl ester hydrochloride, glycyl-3,4-diacetyloxy-L-phenylalanine methyl ester hydrochloride,
3,4-dipivalyloxy-N-(1-methyl-2-acetylvinyl)-L-phenylalanine pivaloyloxymethyl ester,
3,4-dipivalyloxy-N-(1-methyl-2-acetylvinyl)-L-phenylalanine potassium salt,
3,4-diacetyloxy-N-(1-methyl-2-acetylvinyl)-L-phenylalanine potassium salt,
N-formyl-3,4-dipivalyloxy-L-phenylalanine,
N-formyl-3,4-dipivalyloxy-L-phenylalanine pivalyloxy-L-phenylalanine pivaloyloxymethyl ester,
N-formyl-3,4-diacetyloxy-L-phenylalanine,
N-formyl-3,4-diacetyloxy-L-phenylalanine potassium salt, glycyl-3,4-diacetyloxy-L-phenylalanine hydrochloride,
3,4-diacetyloxy-L-phenylalanylglycine hydrochloride,
3,4-dihydroxy-L-phenylalanyl-3,4-dihydroxy-L-phenylalanine hydrochloride,
3,4-diacetyloxy-L-phenylalanyl-3,4-diacetyloxy-L-phenylalanine methyl ester hydrochloride,
3,4-diacetyloxy-L-phenylalanyl-3,4-diacetyloxy-L-phenylalanine benzyl ester hydrochloride,
L-tyrosyl-3,4-dihydroxyphenylalanine,
glycyl-3,4-diacetyloxy-L-phenylalanine benzyl ester hydrochloride,
L-leucyl-3,4-dihydroxyphenylalanine, and
L-3,4-dihydroxyphenylalanine-D-alanine.

7. A method according to claim 6 wherein an L-3,4-dihydroxyphenylalanine decarboxylase inhibitor is administered, together with said active ingredient in a ratio to said L-3,4-dihydroxyphenylalanine or derivative thereof of between 1:100 and 10:1.

8. A method according to claim 7 wherein said inhibitor is L-$\alpha$-hydrazino-3,4-dihydroxy-$\alpha$-methyl-$\beta$-phenylpropionic acid or N-DL-seryl-N'-(2,3,4-trihydroxybenzyl)hydrazine.

9. A method according to claim 6 wherein said amount is from 0.2 mg to 50 mg/kg of body weight of a host animal.

10. A method according to any one of claims 6, 7, 8, or 9 wherein said component (i) is L-3,4-dihydroxyphenylalanine and said component (ii) is L-arginine or D-phenylalanine.

11. A method according to claim 6 or 7 or 8 wherein said amino acid is $\gamma$-aminobutyric acid.

12. A composition according to claim 2 wherein said amino acid is $\gamma$-aminobutyric acid and said inhibitor is L-$\alpha$-hydrazino-3,4-dihydroxy-$\alpha$-methyl-$\beta$-phenylpropionic acid.

13. A composition according to any one of claims 1, 2 or 3 wherein said amino acid is $\gamma$-aminobutyric acid and wherein said component (i) is L-3,4-dihydroxyphenylalanine.

* * * * *